United States Patent [19]

Boutonnat et al.

[11] 4,255,960
[45] Mar. 17, 1981

[54] APPARATUS FOR MEASURING AND/OR MONITORING A CONSTITUENT OF AN ATMOSPHERE

[75] Inventors: Maurice Boutonnat, Gouvieux; Gérard Rose, Villers St-Paul, both of France

[73] Assignee: Charbonnages de France, Paris, France

[21] Appl. No.: 65,204

[22] Filed: Aug. 9, 1979

[30] Foreign Application Priority Data

Aug. 25, 1978 [FR] France .............................. 78 24663

[51] Int. Cl.³ .............................................. G01N 25/18
[52] U.S. Cl. .................................... 73/27 R; 340/632
[58] Field of Search ................ 73/27 R; 340/632, 633

[56] References Cited

U.S. PATENT DOCUMENTS

| | | | |
|---|---|---|---|
| 3,237,181 | 2/1966 | Palmer | 340/633 |
| 4,002,429 | 1/1977 | Bartovsky et al. | 73/27 R X |
| 4,063,447 | 12/1977 | Mathison | 73/27 R |

FOREIGN PATENT DOCUMENTS 2337339  7/1977  France .

*Primary Examiner*—John Petrakes
*Assistant Examiner*—Joseph W. Roskos
*Attorney, Agent, or Firm*—Cushman, Darby & Cushman

[57] ABSTRACT

A measuring cell having a measuring filament and a reference filament is disposed in a cap of sintered metal. A time base circuit, actuated by the closing of a switch, connects the filaments to an electrical supply circuit after a predetermined delay. Subsequently, the time base circuit sequentially triggers the connection of the filaments to a measuring circuit, the storage in a memory of the value of the output signal of the measuring circuit and the display of this stored value, the disconnection of the supply circuit, and the illumination of an end of operation warning lamp. The value displayed is proportional to the amount of a constituent of an atmosphere diffused into the measuring cell. The apparatus can be used as a portable fire damp meter or explosimeter.

9 Claims, 3 Drawing Figures

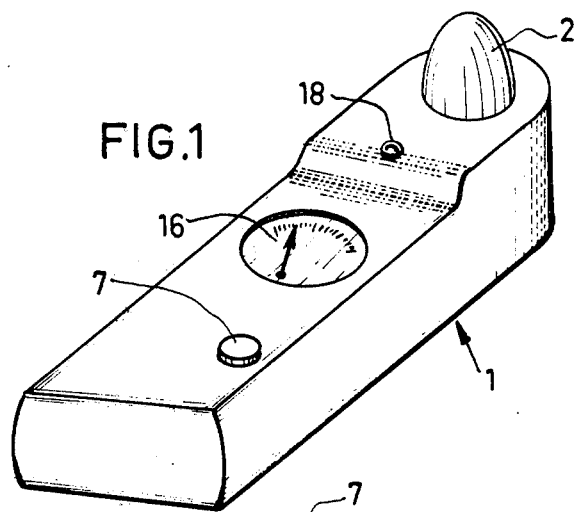
FIG.1
FIG.2
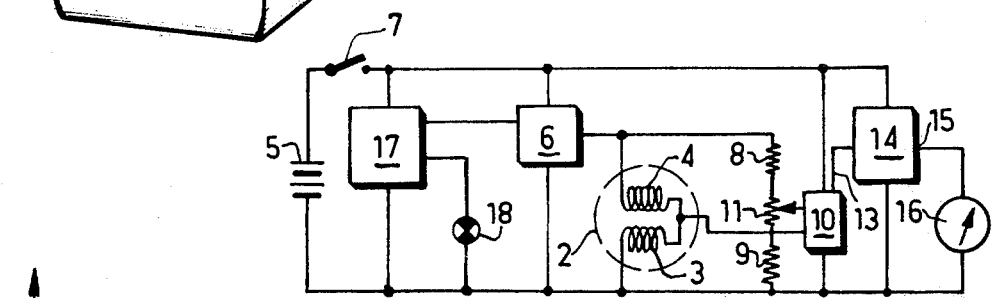
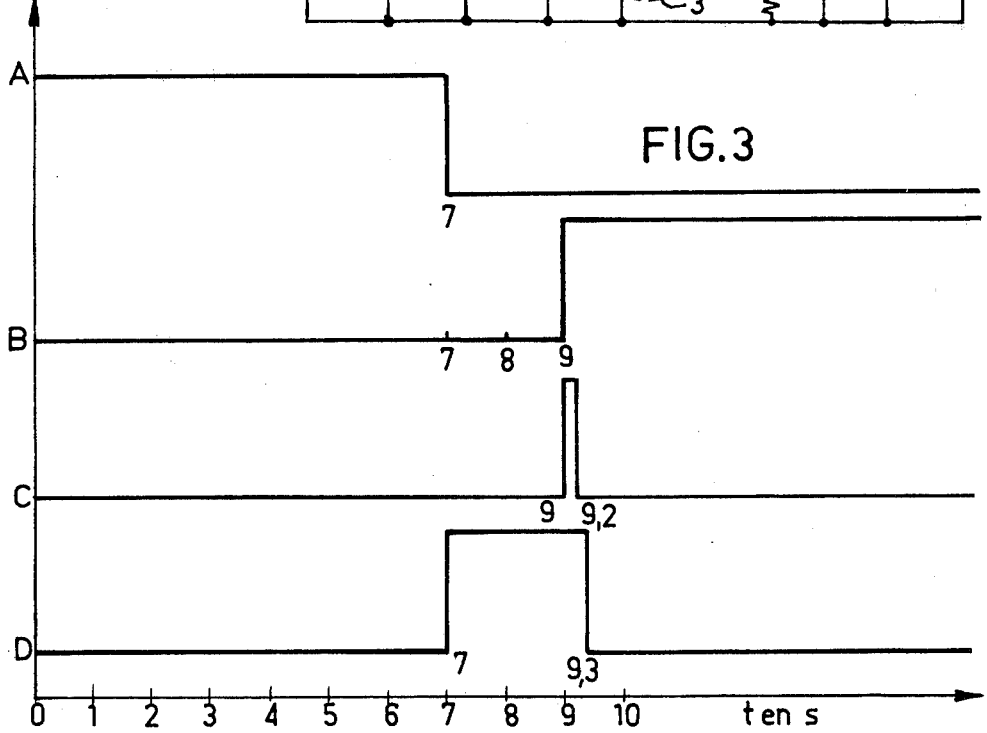
FIG.3

APPARATUS FOR MEASURING AND/OR MONITORING A CONSTITUENT OF AN ATMOSPHERE

BACKGROUND OF THE PRESENT INVENTION

The invention relates to an apparatus for measuring and/or monitoring a constituent of an atmosphere by means of a thermosensitive element fed electrically and disposed in a porous-wall measuring cell.

Measuring and/or monitoring instruments, such as explosimeters, methanometers, katharometers, or other devices for determining constituents of an atmosphere, are known, in which a measuring cell containing at least one electrically heated measuring filament or sensitive element is disposed in the atmosphere. In known automatic instruments which are permanently installed it is known that the display of the value of the amount of the constituent being monitored is subject to a delay due to the diffusion of the atmosphere through the porous wall.

This delay does not usually constitute a serious disadvantage, because the use of such instruments is restricted to the monitoring of places where the variation is slow and the amounts monitored are generally remote from the danger threshold, it being most important to detect an increase in the amount of the monitored constituent, for example in the case of explosimetry.

In addition, U.S. Pat. No. 4,002,429 discloses an intermittent measuring instrument in which the measuring time is delayed in relation to the moment $T_o$ at which a voltage is applied and at which the gas to be measured is introduced. French Pat. No. 2,337,339 (equivalent to U.S. patent application 645,838 now abandoned) describes an intermittent interrogation apparatus in which storage in a memory permits permanent reading of the inflammable gas content. If devices of these kinds were applied to a portable porous-wall cell apparatus, disadvantages would result which will be explained below.

It will first be recalled that the porous-wall cell has two important advantages, namely, that the wall can be made of sintered metal possessing great mechanical strength for the protection of the fragile filament, and that no mechanical means is required for pumping the atmosphere into the measuring cell.

If it is desired to make use of these advantages for a manual measuring instrument, the operator must be given instructions to postpone his reading until the time required for the diffusion of the atmosphere into the cell has expired.

If however, the operator does not conscientiously follow these instructions, or if he is distracted, he may not wait long enough for good diffusion of the gas to occur. This will result in erroneous measurements.

It is an object of this invention to propose an apparatus avoiding this disadvantage and ensuring that the measurement is made at the most convenient moment both for achieving good diffusion of the gas and for obtaining the most accurate reading possible.

SUMMARY

According to the present invention there is provided an apparatus for measuring and/or monitoring the amount of a constituent of an atmosphere comprising a measuring cell having a porous wall for communicating the interior of the cell with said atmosphere, an element having an electrical property which varies in proportion to the amount of said constituent disposed in said measuring cell, an electrical supply circuit for connection to said element, and an electrical measuring circuit for connection to said element, said measuring circuit being arranged to produce an output signal the value of which is proportional to the electrical property of said element and hence to the amount of said constituent, the apparatus further comprising a storage device for storing the value of the output signal, a display device for displaying the stored value, and a triggerable time base including means for sequentially triggering the following operations; connection of said element to the measuring circuit after a predetermined delay, and storage in the storage device of the last value of the output signal.

In an embodiment the time base includes means for triggering the connection of said element to the electrical supply circuit after a predetermined delay, and the connection of said element to the measuring circuit is delayed with respect to its connection to the supply circuit.

Likewise in an embodiment, the time base includes means for limiting the connection time of said element to the supply circuit and/or to the measuring circuit.

In a portable apparatus it is advantageous for the time base to be manually triggerble and to contain means for interrupting or halting the sequence of operations triggered by the time base.

BRIEF DESCRIPTION OF THE DRAWINGS

An embodiment of the present invention will hereinafter e described, by way of example, with reference to the accompanying drawings, in which:

FIG. 1 is a perspective view of a manually controlled portable methanometer or explosimeter unit with builtin battery, FIG. 2 shows the electric circuit diagram of the apparatus of FIG. 1, and FIG. 3 shows a time diagram of the operations controlled by a time base incorporated in the apparatus.

DESCRIPTION OF A PREFERRED EMBODIMENT

An apparatus according to the invention comprises a casing 1 which has a dome 2 of sintered metal inside which are disposed in a manner known per se a measuring filament 3 and a compensator or reference filament 4, the filaments being fed in known manner by an electric battery 5 through a voltage regulator 6 and a switch 7. These filaments are connected in a measuring bridge comprising two fixed resistors 8 and 9 and connected to a measuring circuit 10 by way of a potentiometer 11, once again in a manner known per se. The measuring circuit supplies a measurement signal at an output terminal 13.

According to the invention the apparatus contains a storage device 14 connected to the output terminal 13 of the measuring circuit 10. To the output terminal 15 of the storage device 14 is connected a galvanometric display device 16 for the analogue or digital display of the stored value.

The apparatus also contains a time base circuit 17, which supplies timing signals arranged to sequentially control the connection of the supply circuit 6 to supply electric current to the filaments 3 and 4, the connection of the measuring bridge to the measuring circuit 10, the storage of the value of the output signal of the measuring circuit 10 in the memory 14, the disconnection of the bridge from the measuring circuit 10, and then the disconnection of the filaments from the supply circuit.

This sequence of operations is triggered automatically by the time base circuit 17 as soon as the switch 7 is manually closed, and continues as far as the storage and display of the value as long as the switch 7 is kept closed. When the switch 7 is released it opens and the apparatus is ready for another measuring sequence.

The apparatus also contains a pilot lamp 18 the illumination of which is controlled by the time base circuit at the same time as the storage and display, in order to warn the operator that the measuring sequence has been completed and that he can read the value displayed.

It can be seen that the apparatus possesses the advantages which it was proposed to impart to it. It is easy for an operator to take the apparatus to a place which is within reach, such as a bell in the roof of a mine or gallery or a fault, for the purpose of safely measuring there the content of fire damp or other inflammable gas, the value of this content remaining stored in the memory as long as the switch 7 is not released.

The apparatus can optionally be carried at the end of a rod provided that a second switch connected in parallel with the switch 7 is disposed on the rod, for example with the aid of an electrical connection incorporated in the connection between the rod and the apparatus.

FIG. 3 shows a time diagram of the operations controlled by the time base circuit 17. The time t is plotted in seconds on the abscissa. The moment of time O is assumed to be the moment when the time base circuit 17 is triggered through the closing of the switch 7. The line A corresponds to the diffusion time during which, because of the design, the time base circuit does not trigger any operation. In this embodiment the diffusion time is seven seconds. It is possible to utilize this dead time for checking the voltage of the battery 5 by arranging for the time base circuit to control connection of the galvanometric device 16 to display the voltage during this time.

The line D shows the application of voltage to the measuring bridge, here from 7 to 9.3 seconds.

The line C indicates the connection of the measuring bridge to the measuring circuit 10, here from 9 to 9.2 seconds, that is to say at the end of the voltage application time.

The line B indicates the connection of the measuring circuit to the memory 14, here at 9 seconds.

At the end of the application of the voltage, that is to say at 9.3 seconds, the pilot lamp is illuminated, indicating that the sequence has been completed and that the operator can make the reading.

We claim:

1. An apparatus for measuring and/or monitoring the amount of a constituent of an atmosphere comprising a measuring cell having a porous wall for communicating the interior of the cell with said atmosphere, an element having an electrical property which varies in proportion to the amount of said constituent disposed in said measuring cell, an electrical supply circuit for connection to said element, and an electrical measuring circuit for connection to said element, said measuring circuit being arranged to produce an output signal the value of which is proportional to the electrical property of said element and hence to the amount of said constituent, the apparatus further comprising a storage device for storing the value of the output signal, a display device for displaying the stored value, and a triggerable time base including means for sequentially triggering the following operations; connection of said element to the measuring circuit after a predetermined delay, and storage in the storage device of the last value of the output signal.

2. An apparatus according to claim 1, wherein the time base further includes means for triggering the connection of said element to the electrical supply circuit after a predetermined delay.

3. An apparatus according to claim 2, wherein the connection of said element to the measuring circuit is delayed with respect to the connection of the element to the supply circuit.

4. An apparatus according to claim 2, wherein the time base further includes means for limiting the connection time of said element to the supply circuit and/or to the measuring circuit.

5. An apparatus according to claim 1, wherein the time base is arranged to be manually triggered.

6. An apparatus according to claim 5, further comprising means for interrupting or halting the sequence of operations triggered by the time base.

7. An apparatus according to claim 1 further comprising indicator means for displaying the state of triggering of at least one of the operations.

8. An apparatus according to claim 7, wherein the operation displayed is the storage in the storage device of the last value of the output signal and/or the display of the said value.

9. An apparatus according to claim 1, wherein the electrical supply circuit includes a current source and wherein the time base further includes means for the connection of the current source to the display device for displaying the voltage of the said source before connection of said element to the supply circuit.

* * * * *